United States Patent [19]

Abma et al.

[11] Patent Number: 5,714,626

[45] Date of Patent: Feb. 3, 1998

[54] ORGANIC PEROXIDE STABILIZATION WITH β-DICARBONYL COMPOUNDS

[75] Inventors: Charles Abma, Marshall; Peter Frenkel, Longview; Lawrence Bock, Longview; Anthony Andrews, Longview; Michael Wells, Longview, all of Tex.

[73] Assignee: Witco Corporation, Greenwich, Conn.

[21] Appl. No.: 656,094

[22] Filed: May 31, 1996

[51] Int. Cl.⁶ .................................................. C07C 69/96
[52] U.S. Cl. .......................... 558/264; 526/228; 526/233
[58] Field of Search ........................ 558/264; 526/228, 526/233

[56] References Cited

U.S. PATENT DOCUMENTS 5,155,192  10/1992  Boelema et al. ......................... 526/228

OTHER PUBLICATIONS

Kolczynski et al; Annu. Tech. Conf.,SPI(Soc. Plast.Ind.)Reinf.Plast./Compos.Div.,Proc.,24th(1969), 16–A–1–8Publisher:Soc. of the Plast.Ind;Inc.,New York, N.Y., 1969.

*Primary Examiner*—Paul J. Killos
*Assistant Examiner*—Sreeni Padmanabhan
*Attorney, Agent, or Firm*—Scully, Scott, Murphy & Presser

[57] ABSTRACT

Organic peroxide compositions which contain a β-dicarbonyl compound to retard the rate of decomposition of the peroxide compound are disclosed.

22 Claims, No Drawings

ORGANIC PEROXIDE STABILIZATION WITH β-DICARBONYL COMPOUNDS

BACKGROUND OF THE INVENTION

The present invention relates to organic peroxide compositions, and more specifically to peroxydicarbonate and diacyl peroxide compositions, in which a β-dicarbonyl compound has been added to retard the rate of decomposition of the peroxide compound.

Organic peroxides, such as peroxydicarbonates and diacyl peroxides, are useful as free-radical initiators in the polymerization or copolymerization of ethylenically unsaturated monomers.

For example, organic peroxides are used as initiators in the polymerization of vinyl halides, such as vinyl chloride or vinyl bromide; vinylidene halides such as vinylidene chloride; and other compounds containing polymerizable unsaturated units. The products of this well known polymerization process have extensive commercial applications.

The polymerization of vinyl halides or the copolymerization of vinyl halides with vinylidene halides is usually conducted in an aqueous medium, i.e., emulsion, solution or suspension polymerization. In such polymerizations, the monomer or mixture of monomers is dispersed in water in the presence of a surfactant and thereafter the polymerization initiated with an organic peroxide. This is a well known reaction that has been widely reported.

All organic peroxides are by their nature hazardous materials. Their usefulness depends on their ability to decompose into free radicals, shown by the following reaction:

$$RO\text{---}OR' \rightarrow RO\cdot + R'O\cdot$$

The rate of this decomposition reaction at any given temperature depends on the structure of R and R'.

The decomposition reaction is exothermic. If exothermic decomposition were to occur during production, storage, or shipment, when the peroxides are in a concentrated form, excess pressure development and/or fire or explosion could result. Consequently, many organic peroxides must be kept refrigerated.

There have been several reports in recent years of the retardation of the rate of decomposition of organic peroxides.

The Journal of The American Chemical Society, Volume 72, pages 1254 to 1263 (1950), discloses the use of, for example, ethyl acetoacetate, iodine, trinitrobenzene, acetanilide, nitromethane, phenol, hydrogen peroxide, and tetralin to retard the rate of decomposition of diisopropyl peroxydicarbonate.

U.S. Pat. No. 4,515,929 (1985) reports aqueous dispersions of organic peroxides including peroxydicarbonates, which are stabilized against decomposition by the addition of diphenyl peroxydicarbonate or di(alkyl substituted) phenyl peroxydicarbonates.

U.S. Pat. No. 4,552,682 (1985) discloses the use of phenolic antioxidants to retard the rate of degradation of aqueous organic peroxide dispersions. The use of phenolic antioxidants is undesirable because they result in discoloration.

U.S. Pat. No. 5,155,192 (1992) discloses the use of organic hydroperoxides, e.g., tert-butyl hydroperoxide, to retard the rate of decomposition of peroxydicarbonates.

Research Disclosure, April, 1995, page 275, reports the thermal stabilization of dialkyl peroxydicarbonates using unsaturated nitriles or unsaturated acetylenic compounds.

SUMMARY OF THE INVENTION

The present invention relates to the use of certain non-peroxide compounds which are effective in retarding the decomposition of organic peroxides such as peroxydicarbonates and diacyl peroxides. Thus, one aspect of the present invention is a composition containing an organic peroxide compound selected from the group consisting of peroxydicarbonate and diacyl peroxide compounds and at least one β-dicarbonyl compound which reduces the rate of decomposition of the peroxide. Another aspect of the present invention is the method of stabilizing a peroxydicarbonate or diacyl peroxide against decomposition, comprising adding thereto a β-dicarbonyl compound in an amount effective to achieve said stabilization.

In particular, β-dicarbonyl compounds useful in the present invention include those of formulas I, II and III:

$$R^5\text{---}C(O)\text{---}CHR^6\text{---}C(O)\text{---}R^7 \quad (III)$$

wherein
 m is 1–5
 n is 1–6,
 i is 0–1,
 x is 0–2 n,
 y is 0–2 m,
$R^1$ is alkyl containing 1 to 22 carbon atoms, phenyl, or phenyl substituted with one or more of alkyl containing 1 to 22 carbon atoms, halogen, and hydroxy, and $R^1$ can be hydrogen where i is zero,
$R^2$ is alkyl containing 1 to 22 carbon atoms, phenyl, or phenyl substituted with one or more of alkyl containing 1 to 22 carbon atoms, halogen, and hydroxy, and when x is greater than 1, each occurrence of $R^2$ can be the same or different and can be on the same or different ring carbon atoms;
$R^3$ is hydrogen, alkyl containing 1 to 22 carbon atoms, acyl containing 2 to 22 carbon atoms, phenyl, or phenyl substituted with one or more of alkyl containing 1 to 22 carbon atoms, halogen, and hydroxy;
$R^4$ is alkyl containing 1 to 22 carbon atoms, phenyl, or phenyl substituted with one or more of alkyl containing 1 to 22 carbon atoms, halogen, and hydroxy, and when y is greater than 1, each occurrence of $R^4$ can be the same or different and can be on the same or different ring carbon atoms;
$R^5$ is hydrogen, alkyl containing 1 to 22 carbon atoms, phenyl, or phenyl substituted with one or more of alkyl containing 1 to 22 carbon atoms, halogen, and hydroxy;
$R^6$ is hydrogen or alkyl containing 1 to 22 carbon atoms, phenyl or phenyl substituted with one or more of alkyl containing 1 to 22 carbon atoms, halogen, and hydroxy; or
$R^6$ is ---C(O) $OR^8$ or ---C(O)$R^8$ wherein $R^8$ is alkyl containing 1 to 22 carbon atoms; and
$R^7$ is phenyl or alkyl containing 1 to 22 carbon atoms.

DETAILED DESCRIPTION OF THE INVENTION

The present invention relates to compositions containing an organic peroxide, which is a peroxydicarbonate or a diacyl peroxide, and at least one β-dicarbonyl stabilizing compound to retard the rate of decomposition of the peroxide compound.

β-dicarbonyl compounds useful in the present invention may be of one of the following general formulas:

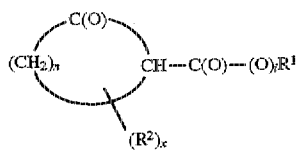

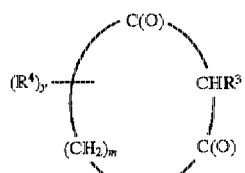

In Formula (I), n is 1–6 and preferably 3–5; x is zero up to 2 n and i is 0–1; and $R^1$ is phenyl, substituted phenyl or alkyl containing 1 to 22 carbon atoms, and preferably 1 to 5 carbon atoms. The phrase "substituted phenyl" refers to phenyl substituted with alkyl containing 1 to 22 carbon atoms, halogen (i.e. fluorine, chlorine, bromine, and/or iodine), and/or hydroxy, or with any two or more of any such groups. That is, when two or more of such substituents are present they can be the same or different. The $R^2$ group can be phenyl, substituted phenyl or alkyl containing 1 to 22 carbon atoms and preferably 1 to 5 carbon atoms.

In Formula (II), m is 1–5 and preferably 2–4, y is zero up to 2 m and $R^3$ can be hydrogen, phenyl or substituted phenyl. Alternatively, $R^3$ can be alkyl containing 1 to 22 carbon atoms and preferably 1 to 5 carbon atoms, or $R^3$ can be acyl containing 2 to 22 carbon atoms. The $R^4$ substituent can be phenyl, substituted phenyl, or alkyl containing 1 to 22 carbon atoms and preferably 1 to 5 carbon atoms.

In Formula (III), $R^5$ can be hydrogen, phenyl, substituted phenyl, or $R^5$ can be alkyl containing 1 to 22 carbon atoms and preferably 1 to 5 carbon atoms. $R^7$ can be phenyl, or $R^7$ can be alkyl containing 1 to 22 carbon atoms and preferably 1 to 5 carbon atoms. The $R^6$ group can be hydrogen, phenyl, substituted phenyl or can be alkyl containing 1 to 22 carbon atoms and preferably 1 to 5 carbon atoms. Also $R^6$ can be —C(O)O$R^8$ or —C(O)$R^8$; in these cases, $R^8$ is alkyl containing 1 to 22 carbon atoms and preferably 1 to 5 carbon atoms.

In all cases, alkyl substituents can be straight-chain; branched; cycloalkyl or cycloalkylalkyl. The cycloalkyl structure in the latter two cases may optionally be alkyl substituted.

Preferred embodiments useful in the present invention include cyclic ketone carboxylate compounds of Formula (I) such as ethyl-2-cyclopentanone carboxylate (wherein n is 3, i is 1, x is 0, and $R^1$ is ethyl), ethyl-2-cyclohexanone carboxylate (wherein n is 4, i is 1, x is 0, and $R^1$ is ethyl), methyl-2-cycloheptanone carboxylate (wherein n is 5, i is 1, x is 0, and $R^1$ is methyl), and ethyl-4-methyl-2-cyclohexanone-1-carboxylate (n is 4, i is 1, x is 1, $R^1$ is ethyl and $R^2$ is 4-methyl).

Other preferred embodiments of Formula (I) useful in the present invention include cyclic-β-diketones in which one of the carbonyl groups is contained in a cyclic structure, such as 2-acetyl cyclopentanone (wherein n is 3, i is 0, x is 0, and $R^1$ is methyl) and 2-acetyl cyclohexanone (n is 4, i is 0, x is 0, and $R^1$ is methyl).

Preferred embodiments useful in the present invention include compounds of Formula (II), such as 1,3-cyclohexanedione (m is 3, y is 0, and $R^3$ is H) and 1,3-cyclopentanedione (m is 2, y is 0, and $R^3$ is H).

Additional preferred embodiments useful in the present invention include compounds of Formula (III). Examples of such compounds include 2,4-pentanedione (wherein $R^5$ is methyl, $R^6$ is H, and $R^7$ is methyl) and dibenzoyl methane ($R^5$ and $R^7$ are phenyl, and $R^6$ is —H).

β-dicarbonyl compounds of Formulas (I), (II) or (III) are commercially available and/or can be synthesized from commercially available starting materials by use of procedures familiar to one of the ordinary skill in the art.

The amount of β-dicarbonyl to use in the compositions and methods of the present invention is an amount sufficient to retard the rate of decomposition of the peroxide compound. The preferred amount of β-dicarbonyl is a concentration of 0.2–5.0% by weight of the peroxydicarbonate or diacyl peroxide present. The exact amount will vary and depend on both the peroxide compound and the β-dicarbonyl used, and on the conditions to which the peroxide composition is exposed.

Peroxide compounds with which this invention is particularly useful are of the general structural formula:

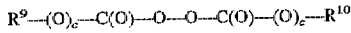

where each c is 0 or 1, and $R^9$ and $R^{10}$ can each be an aliphatic, cycloaliphatic or aromatic group with 1 to 22 carbon atoms, preferably 2 to 8 carbon atoms. When the subscripts c are zero, the compound is a diacyl peroxide, and when the subscripts c are one, the compound is a peroxydicarbonate. $R^9$ and $R^{10}$ may be branched or non-branched, substituted or unsubstituted alkyl, alkenyl, cycloalkyl or aromatic groups.

Examples of $R^9$ and $R^{10}$ groups include phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

Specific examples of peroxydicarbonates include diethyl peroxydicarbonate, di-n-butyl peroxydicarbonate, diisobutyl peroxydicarbonate, and di-4-tert-butylcyclohexyl peroxydicarbonate. Preferably the peroxydicarbonate is di-sec-butyl peroxydicarbonate, di-2-ethylhexyl peroxydicarbonate, di-n-propyl peroxydicarbonate or diisopropyl peroxydicarbonate.

Specific examples of diacyl peroxides include benzoyl peroxide, dilauroyl peroxide, didecanoyl peroxide, diacetyl peroxide, and di(3,5,5-trimethylhexanoyl) peroxide.

The peroxide compound may be symmetrical or unsymmetrical i.e., $R^9$ and $R^{10}$ may be the same or different. The peroxide may be a homogeneous mixture containing symmetric peroxides, asymmetric peroxides such as isopropyl-sec-butyl peroxydicarbonate or 2-methylpropionyl-3-methylpentanoyl peroxide or a mixture of symmetric and asymmetric peroxides such as mixtures of diisopropyl peroxydicarbonate, di-sec-butyl peroxydicarbonate and isopropyl-sec-butyl peroxydicarbonate as disclosed in U.S. Pat. No. 4,269,726.

The peroxydicarbonate compounds and diacyl peroxide compounds can be synthesized by conventional techniques familiar to one of ordinary skill in the art. Peroxydicarbonates are typically prepared by reacting the corresponding alkyl chloroformate with aqueous sodium peroxide at low temperatures, 0°–20° C. See U.S. Pat. No. 2,370,588 and the Journal of the American Chemical Society, Volume 72, page 1254 (1950). Diacyl peroxides are typically made from acid chlorides using synthetic techniques familiar to one of ordinary skill in the art.

Preferably, the peroxydicarbonates and diacyl peroxides with which this invention is useful include those which are a liquid at 0° C. and more preferably a liquid at −5° C. Still more preferred are the peroxydicarbonates and diacyl peroxides which are liquid down to −20° C.

The present invention is especially applicable to aqueous dispersions of peroxydicarbonates and diacyl peroxides that are useful as initiators in the free radical polymerization of ethylenically unsaturated materials, particularly in an aqueous medium, e.g., suspension or emulsion polymerization. A dispersion of the peroxide is prepared by dispersing it in water with a suitable dispersing aid, e.g., a surfactant or emulsifying agent. Surfactants and emulsifying agents useful in the formulation of such dispersions are well known in this field and are quite numerous.

To prepare dispersions in accordance with the present invention, the β-dicarbonyl compound may be added to an already-formed peroxide dispersion, or to the water containing the surfactant, or to the peroxide before the dispersion is formed. Dispersions of the present invention generally contain 20 to 70% by weight, preferably 30 to 60% by weight, of the peroxydicarbonate compound or diacyl peroxide and 0.2 to 5% (by weight of the peroxide) of the β-dicarbonyl.

The manner of preparation of peroxide dispersions is known to one of ordinary skill in the art. A description of peroxydicarbonate dispersions and their preparation can be found in U.S. Pat. No. 4,515,929; U.S. Pat. No. 3,825,509; U.S. Pat. No. 3,988,261 and U.S. Pat. No. 4,092,470.

Peroxide compositions of the present invention may also be prepared as physical mixtures in the form of liquids, granules, powders or flakes. A physical mixture in accordance with the present invention may be prepared by mixing a liquid peroxide compound or a solution of a peroxide in a suitable solvent with the desired amount of β-dicarbonyl in a conventional mixing apparatus. The resulting mixture is then, if desired, granulated, pulverized or flaked. The β-dicarbonyl may be added either (1) to the chloroformate- or acid chloride-containing reaction mixture before preparation of the peroxide compound or (2) to the unprocessed reaction mixture immediately after the preparation of the peroxide compound. Either (1) or (2) will ensure that the two components are mixed as homogeneously as possible in order to receive the greatest possible benefit from the stabilizing effect of the β-dicarbonyl.

A solution of the present invention may be prepared by combining the desired amounts of β-dicarbonyl compound and peroxide in a suitable solvent.

Suitable organic solvents include those normally employed for peroxydicarbonate or diacyl peroxides, such as esters of phthalic acid, an example of which is dibutyl phthalate, and aliphatic and aromatic hydrocarbons and mixtures of such hydrocarbons, examples of which are hexane, odorless mineral spirits, mineral oil, benzene, toluene, xylene and (iso)paraffins such as isododecane. Other suitable solvents will be familiar to one of ordinary skill in the art.

Solutions according to the present invention preferably contain at least 10% by weight and more preferably at least 25% by weight of a peroxydicarbonate or diacyl peroxide compound.

The peroxide compositions of the present invention display numerous significant advantages. Chief among these is improved thermal stability, both in response to exposure to elevating temperature and in response to a given constant temperature. Thermal stability of self-reactive substances, in response to elevating temperatures, can be determined by measuring the self accelerating decomposition temperature (SADT). SADT is one of the recognized characteristics for determining the safe storage and transportation of materials such as organic peroxides. [Recommendations on the Transport of Dangerous Goods, 9th ed., United Nations, N.Y. 1995, Section 11.3.5, page 264].

SADT can be directly correlated with the onset temperature as measured in a differential thermal analyzer (DTA). The onset temperature is the point at which an uncontrolled thermal decomposition starts. The onset temperature can be measured by determining the point at which the rate of temperature increase in a sealed cell exceeds a certain predetermined value. In addition, the onset temperature can be measured by determining the point at which the rate of pressure increase in the sealed cell exceeds a certain predetermined value.

Thermal stability in response to a given constant temperature can be assessed by means of accelerated aging tests at, for instance, 15° C.

The β-dicarbonyl compounds of the present invention increase the onset temperature of both peroxydicarbonates and diacyl peroxides.

Also, the β-dicarbonyl compounds do not detract from the effectiveness of the peroxide as a polymerization initiator.

The following examples are intended to illustrate the claimed invention and are not in any way designed to limit its scope. Numerous additional embodiments within the scope and spirit of the claimed invention will become apparent to those skilled in the art.

EXAMPLE 1

The onset temperature was measured and compared for samples of pure di-2-ethylhexyl peroxydicarbonate and samples of di-2-ethylhexyl peroxydicarbonate in the presence of each of several different β-dicarbonyl compounds. The liquid mixtures were prepared by dissolving the required amount of β-dicarbonyl in the peroxydicarbonate.

Using a type of Differential Thermal Analyzer (Radex Solo Thermal Analyzer, marketed by Astra Scientific International, Pleasanton, Calif.), with an isothermal hold temperature of 30° C. for 15 minutes and then a temperature increase of 1°/minute to 130° C., the onset temperature was measured for a one gram sample of di-2-ethylhexyl peroxydicarbonate in a sealed cell.

The onset temperature was measured both by noting the point where the rate of increase (ΔT) of the sample temperature reached 0.2° C./minute and also the point where the rate of increase in pressure (ΔP) of the closed sample cell reached 1.0 psi/minute. ΔT is the difference between the oven temperature and the sample temperature. ΔP is the difference between a reference pre-calibrated pressure and the pressure developed in the sealed sample cell.

The procedure was repeated with separate samples of the above peroxydicarbonate containing, in turn, ethyl-2-cyclohexanone carboxylate, 2-acetyl cyclohexanone, 2-acetyl cyclopentanone, and 2,4-pentanedione. The results are shown in Table I. Results obtained with ethyl acetoacetate, which is disclosed in the prior art, are included for comparison.

The results show that the presence of a β-dicarbonyl compound in accordance with the present invention increases the temperature at which self accelerating decomposition of the peroxydicarbonate will begin. This shows that the β-dicarbonyl compound is an effective stabilizer and is superior to ethyl acetocetate. The results also show that the effect is concentration dependent, with the decomposition beginning at a higher temperature when more β-dicarbonyl compound is present.

TABLE I

ONSET TEMPERATURE FOR
98.3% DI-2-ETHYLHEXYL PEROXYDICARBONATE

| ADDITIVE | Additive Wt % | Onset Temperature (°C.) by ΔT | by ΔP |
|---|---|---|---|
| None | ---- | 37.3 | 40.2 |
| Ethyl acetoacetate | 2.9 | 43.9 | 46.9 |
| Ethyl-2-cyclohexanone carboxylate | 0.9 | 49.1 | 50.8 |
| Ethyl-2-cyclohexanone carboxylate | 2.9 | 55.2 | 57.0 |
| 2,4-Pentanedione | 2.9 | 55.3 | 58.2 |
| 2-Acetyl cyclohexanone | 2.9 | 55.6 | 57.5 |
| 2-Acetyl cyclopentanone | 3.1 | 57.7 | 61.2 |

EXAMPLE 2

The onset temperatures for samples of di-2-ethylhexyl peroxydicarbonate diluted with odorless mineral spirits (OMS) and samples of di-2-ethylhexyl peroxydicarbonate diluted in OMS in the presence of several different β-dicarbonyl compounds were measured and compared.

The liquid mixtures were prepared by dissolving the indicated amount of β-dicarbonyl compound in the peroxydicarbonate solution.

Using the same apparatus and procedure as described in Example 1, the onset temperature for a one gram sample of 82.5% di-2-ethylhexyl peroxydicarbonate diluted in OMS was measured. The procedure was repeated with separate samples of the above solution to which ethyl-2-cyclohexanone carboxylate, 2-acetyl cyclohexanone, 2-acetyl cyclopentanone, methyl-2-cycloheptanone carboxylate, ethyl-2-oxocyclopentane carboxylate, dibenzoyl methane, and ethyl-4-methyl-2-cyclohexanone-1-carboxylate had been added. The results are shown in Table II. Results obtained with ethyl acetoacetate, which is disclosed in the prior art, are included for comparison.

As can be seen in Table II, the addition of a β-dicarbonyl compound in accordance with the present invention increases the temperature at which self accelerating decomposition of the peroxydicarbonate will begin. The results also show that the effect is concentration dependent, with the decomposition of the peroxydicarbonate beginning at a higher temperature when more β-dicarbonyl compound is present.

TABLE II

ONSET TEMPERATURE FOR
82.5% DI-2-ETHYLHEXYL PEROXYDICARBONATE IN OMS

| ADDITIVE | Additive Wt % | ONSET TEMPERATURE (°C.) by ΔT | by ΔP |
|---|---|---|---|
| None | ---- | 42.9 | 43.3 |
| Ethyl acetoacetate | 3.1 | 43.4 | 47.5 |
| Ethyl-2-cyclohexanone carboxylate | 0.2 | 43.1 | 46.0 |
| Ethyl-2-cyclohexanone carboxylate | 0.5 | 47.5 | 48.0 |
| Ethyl-2-cyclohexanone carboxylate | 1.0 | 50.0 | 51.6 |
| Ethyl-2-cyclohexanone carboxylate | 2.4 | 55.1 | 54.7 |
| Ethyl-2-cyclohexanone carboxylate | 5.0 | 58.6 | 57.4 |
| 2-Acetyl cyclohexanone | 1.0 | 51.9 | 51.5 |
| 2-Acetyl cyclohexanone | 1.9 | 54.8 | 56.7 |
| 2-Acetyl cyclohexanone | 3.0 | 57.5 | 57.1 |
| 2-Acetyl cyclopentanone | 1.0 | 54.0 | 55.3 |
| 2-Acetyl cyclopentanone | 1.9 | 57.4 | 57.9 |
| 2-Acetyl cyclopentanone | 2.8 | 58.4 | 59.0 |
| Methyl-2-cycloheptanone carboxylate | 1.1 | 44.7 | 47.0 |
| Ethyl-2-oxocyclopentane carboxylate | 1.1 | 47.2 | 47.2 |
| Dibenzoyl methane | 3.0 | 50.0 | 51.5 |
| Ethyl-4-methyl-2-cyclohexanone-1-carboxylate | 3.0 | 55.5 | 57.0 |

EXAMPLE 3

The onset temperatures for samples of di-sec-butyl peroxydicarbonate diluted in odorless mineral spirits (OMS) and samples of di-sec-butyl peroxydicarbonate diluted in OMS in the presence of several different β-dicarbonyl compounds were measured and compared. The liquid mixtures were prepared by dissolving the indicated amount of β-dicarbonyl compound in the peroxydicarbonate solution. The onset temperature was measured according to the procedure described in Example I.

As can be seen in Table III, the addition of a β-dicarbonyl compound in accordance with the present invention increases the temperature at which self accelerating decomposition of the peroxydicarbonate will begin. The results also show that the effect is concentration dependent, with the reaction beginning at a higher temperature when more β-dicarbonyl compound is present. The effect of ethyl acetoacetate is included for comparison.

TABLE III

ONSET TEMPERATURE FOR
75.5% DI-SEC-BUTYL PEROXYDICARBONATE IN OMS

| ADDITIVE | WT % | ONSET TEMPERATURE (°C.) by ΔT | by ΔP |
|---|---|---|---|
| None | ---- | 40.8 | 44.1 |
| Ethyl acetoacetate | 2.9 | 38.2 | 43.6 |
| Ethyl-2-cyclohexanone carboxylate | 1.1 | 46.8 | 47.3 |
| Ethyl-2-cyclohexanone carboxylate | 3.0 | 52.3 | 51.5 |
| 2-Acetyl cyclohexanone | 0.9 | 47.5 | 47.5 |
| 2-Acetyl cyclohexanone | 2.8 | 52.5 | 53.3 |
| 2-Acetyl cyclopentanone | 0.9 | 48.1 | 48.1 |
| 2-Acetyl cyclopentanone | 2.9 | 54.3 | 54.3 |
| 2,4-Pentanedione | 3.0 | 50.5 | 51.6 |

EXAMPLE 4

The effect of the presence of various β-dicarbonyl compounds on the storage stability at 15° C. of pure di-2- ethylhexyl peroxydicarbonate was determined as an accelerated aging test.

The purity of the peroxydicarbonate was measured initially, after 7 days, and after 14 days. The results are presented in Table IV. Ethyl acetoacetate is included as an example of the prior art. The initial purity values were corrected for the presence of the additive.

A similar procedure was repeated with a sample of di-2-ethylhexyl peroxydicarbonate in OMS and a sample of di-sec-butyl peroxydicarbonate in OMS. The results are shown in Tables IV-A and IV-B, respectively. The initial purity values were corrected for the presence of the additive.

The results show that the presence of a β-dicarbonyl compound in accordance with the present invention retards the rate of decomposition of the peroxydicarbonate.

TABLE IV

PURITY VS TIME AT 15° C. FOR
PURE DI-2-ETHYLHEXYL PEROXYDICARBONATE

| | | Purity (%) | | |
|---|---|---|---|---|
| ADDITIVE | Additive Wt % | START | 7 DAYS | 14 DAYS |
| None | — | 98.3 | 32.1 | 17.5 |
| Ethyl acetoacetate | 2.9 | 95.4 | 41.6 | 21.3 |
| Ethyl-2-cyclohexanone carboxylate | 1.1 | 97.3 | 70.4 | 30.4 |
| Ethyl-2-cyclohexanone carboxylate | 2.9 | 95.4 | 88.0 | 61.6 |
| 2-Acetyl cyclohexanone | 1.0 | 97.3 | 43.7 | n.d. |
| 2-Acetyl cyclohexanone | 2.9 | 95.2 | 58.8 | n.d. |
| 2-Acetyl cyclopentanone | 1.0 | 97.3 | 56.3 | n.d. |
| 2-Acetyl cyclopentanone | 3.0 | 95.4 | 71.2 | 43.3 |
| 2,4-Pentanedione | 2.9 | 95.4 | 78.1 | 57.2 | n.d. = not determined

TABLE IV-A

PURITY VS TIME AT 15° C. FOR
DI-2-ETHYLHEXYL PEROXYDICARBONATE IN OMS

| | | Purity (%) | | |
|---|---|---|---|---|
| ADDITIVE | Additive WT % | START | 7 DAYS | 14 DAYS |
| None | — | 76.2 | 33.8 | 24.9 |
| Ethyl-2-cyclohexanone carboxylate | 3.0 | 73.9 | 67.3 | 37.6 |
| 2-Acetyl cyclohexanone | 2.9 | 74.0 | 57.4 | 28.3 |
| 2-Acetyl cyclopentanone | 2.9 | 73.9 | 63.6 | 44.2 |
| 2,4-Pentanedione | 3.0 | 73.9 | 61.0 | 44.9 |

TABLE IV-B

PURITY VS TIME AT 15° C. FOR
DI-SEC-BUTYL PEROXYDICARBONATE IN OMS

| | | Purity (%) | |
|---|---|---|---|
| ADDITIVE | Additive Wt % | START | 7 DAYS |
| None | — | 75.5 | 49.6 |
| Ethyl-2-cyclohexanone carboxylate | 3.1 | 73.2 | 60.8 |
| 2-Acetyl cyclohexanone | 3.2 | 73.1 | 53.3 |
| 2-Acetyl cyclopentanone | 2.8 | 73.5 | 56.9 |

EXAMPLE 5

The onset temperatures for a sample of di-(3,5,5-trimethylhexanoyl) peroxide and samples of di-(3,5,5-trimethylhexanoyl) peroxide in the presence of several different β-dicarbonyl compounds were measured and compared. The liquid mixtures were prepared by dissolving the indicated amount of β-dicarbonyl compound in the peroxide.

Using the procedure described in Example 1, the onset temperature for a sample of 99% di-(3,5,5-trimethylhexanoyl) peroxide was measured. The procedure was repeated with separate samples of the above product to which 2,4-pentanedione and ethyl-2-cyclohexanone carboxylate had been added. The results are shown in Table V.

As can been seen in Table V, the addition of β-dicarbonyl compound in accordance with the present invention increases the temperature at which self accelerating decomposition of the diacyl peroxide will begin.

TABLE V

ONSET TEMPERATURE FOR
99% DI(3,5,5-TRIMETHYLHEXANOYL) PEROXIDE

| | Additive | Onset Temperature (°C.) | |
|---|---|---|---|
| ADDITIVE | WT % | by ΔT | by ΔP |
| None | — | 68.2 | 67.7 |
| 2,4-pentanedione | 3.1 | 68.4 | 70.9 |
| Ethyl-2-cyclohexanone carboxylate | 3.0 | 69.8 | 68.7 |

EXAMPLE 6

The onset temperatures for a sample of di-(3,5,5-trimethylhexanoyl) peroxide diluted in odorless mineral spirits (OMS) and samples of di-(3,5,5-trimethylhexanoyl) peroxide in OMS in the presence of several different β-dicarbonyl compounds were measured and compared. The liquid mixtures were prepared by dissolving the indicated amount of β-dicarbonyl compound in the peroxide solution.

Using the procedure described in Example 1, the onset temperature for a sample of 60% di-(3,5,5-trimethylhexanoyl) peroxide in OMS was measured. The procedure was repeated with separate samples of the above solution to which 2,4-pentanedione and ethyl-2-cyclohexanone carboxylate had been added. The results are shown in Table VI.

As can been seen in Table VI, the addition of β-dicarbonyl compound in accordance with the present invention increases the temperature at which self accelerating decomposition of the diacyl peroxide solution will begin.

TABLE VI

ONSET TEMPERATURE FOR
60% DI(3,5,5-TRIMETHYLHEXANOYL) PEROXIDE IN OMS

| | Additive | Onset Temperature (°C.) | |
|---|---|---|---|
| ADDITIVE | WT % | by ΔT | by ΔP |
| None | — | 74.9 | 76.1 |
| 2,4-pentanedione | 3.0 | 76.3 | 78.1 |
| Ethyl-2-cyclohexanone carboxylate | 3.0 | 76.4 | 77.5 |

We claim:

1. A composition comprising:
   a. an organic peroxide component selected from the group consisting of peroxydicarbonate compounds, diacyl peroxides, and mixtures thereof; and
   b. a sufficient amount of a stabilizer to retard the rate of decomposition of the organic peroxide component, wherein said stabilizer is selected from the group consisting of β-dicarbonyl compounds of formulas I, II and III:

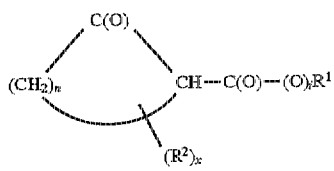

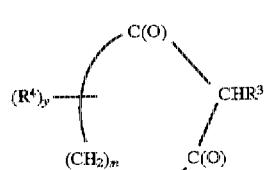

and mixtures thereof, wherein m is 1–5,
n is 1–6,
i is 0–1,
x is 0–2 n,
y is 0–2 m, $R^1$ is alkyl containing 1 to 22 carbon atoms, phenyl, or phenyl substituted with one or more of alkyl containing 1 to 22 carbon atoms, halogen, and hydroxy, and $R^1$ can be hydrogen where i is zero, $R^2$ is alkyl containing 1 to 22 carbon atoms, phenyl, or phenyl substituted with one or more of alkyl containing 1 to 22 carbon atoms, halogen, and hydroxy, and when x is greater than 1, each occurrence of $R^2$ can be the same or different and can be on the same or different ring carbon atoms, $R^3$ is hydrogen, alkyl containing 1 to 22 carbon atoms, acyl containing 2 to 22 carbon atoms, phenyl, or phenyl substituted with one or more of alkyl containing 1 to 22 carbon atoms, halogen, and hydroxy;

$R^4$ is alkyl containing 1 to 22 carbon atoms, phenyl, or phenyl substituted with one or more of alkyl containing 1 to 22 carbon atoms, halogen, and hydroxy; and when y is greater than 1, each occurrence of $R^4$ can be the same or different and can be on the same or different ring carbon atoms;

$R^5$ is hydrogen, alkyl containing 1 to 22 carbon atoms, phenyl, or phenyl substituted with one or more of alkyl containing 1 to 22 carbon atoms, halogen, or hydroxy;

$R^6$ is hydrogen or alkyl containing 1 to 22 carbon atoms, phenyl, or phenyl substituted with one or more of alkyl containing 1 to 22 carbon atoms, halogen, or hydroxy; or $R^6$ can be $-C(O)OR^8$ or $-C(O)R^8$ wherein $R^8$ is alkyl containing 1 to 22 carbon atoms; and $R^7$ is phenyl or alkyl containing 1 to 22 carbon atoms.

2. A composition according to claim 1 comprising a β-dicarbonyl compound of formula (I).

3. A composition according to claim 1 comprising a β-dicarbonyl compound of formula (II).

4. A composition according to claim 1 comprising a β-dicarbonyl compound of formula (III).

5. A composition according to claim 1 wherein said organic peroxide component comprises at least one compound of the formula (IV)

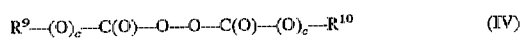

wherein $R^9$ and $R^{10}$ are independently aliphatic, cycloaliphatic or aromatic groups containing 1 to 22 carbon atoms, and c is zero or one.

6. A composition according to claim 5 wherein in formula (IV) both subscripts c are one.

7. A composition according to claim 5 wherein in formula (IV) both subscripts c are zero.

8. A composition according to claim 5 wherein $R^9$ and $R^{10}$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

9. A composition according to claim 1 wherein said stabilizer is selected from the group consisting of ethyl-2-cyclopentanone carboxylate, methyl-2-cycloheptanone carboxylate, ethyl-2-cyclohexanone carboxylate, 2-acetyl cyclopentanone, 2-acetyl cyclohexanone, ethyl-4-methyl-2-cyclohexanone-1-carboxylate, 1,3-cyclohexanedione, 1,3-cyclopentanedione, 2,4-pentanedione and dibenzoyl methane, and mixtures thereof.

10. A composition according to claim 1 wherein said stabilizer comprises 0.2 to 5% by weight of said organic peroxide component.

11. A composition according to claim 1 wherein said organic peroxide component is selected from the group consisting of di-2-ethylhexyl peroxydicarbonate, di-sec-butyl peroxydicarbonate, diethyl peroxydicarbonate, di-n-butyl peroxydicarbonate, isopropyl-sec-butyl peroxydicarbonate, di-4-tert-butylcyclohexyl peroxydicarbonate, di-n-propyl peroxydicarbonate, di-isopropyl peroxydicarbonate, benzoyl peroxide, dilauroyl peroxide, didecanoyl peroxide, diacetyl peroxide, 2-methylpropionyl-3-methylpentanoyl peroxide, and di-(3,5,5-trimethylhexanoyl) peroxide and mixtures thereof.

12. The method of retarding the rate of decomposition of an organic peroxide selected from the group consisting of peroxydicarbonate and diacyl peroxide compounds and mixtures thereof comprising adding to said organic peroxide a stabilizer in an amount thereof effective to retard the rate of said decomposition, wherein said stabilizer is selected from the group consisting of β-dicarbonyl compounds of formulas I, II and III:

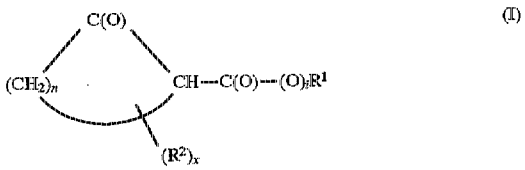

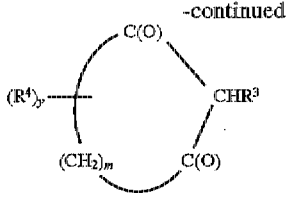

-continued (II)

$$R^5-C(O)-CHR^6-C(O)-R^7 \quad (III)$$

and mixtures thereof, wherein m is 1–5, n is 1–6, i is 0–1, x is 0–2 n, y is 0–2 m, $R^1$ is alkyl containing 1 to 22 carbon atoms, phenyl, or phenyl substituted with one or more of alkyl containing 1 to 22 carbon atoms, halogen and hydroxy, and $R^1$ can be hydrogen where i is zero, $R^2$ is alkyl containing 1 to 22 carbon atoms, phenyl, or phenyl substituted with one or more of alkyl containing 1 to 22 carbon atoms, halogen and hydroxy, and when x is greater than 1, each occurrence of $R^2$ can be the same or different and can be on the same or different ring carbon atoms, $R^3$ is hydrogen, alkyl containing 1 to 22 carbon atoms, acyl containing 2 to 22 carbon atoms, phenyl, or phenyl substituted with one or more of alkyl containing 1 to 22 carbon atoms, halogen, and hydroxy;

$R^4$ is alkyl containing 1 to 22 carbon atoms, phenyl, or phenyl substituted with one or more of alkyl containing 1 to 22 carbon atoms, halogen and hydroxy, and when y is greater than 1, each occurrence of $R^4$ can be the same or different and can be on the same or different ring carbon atoms;

$R^5$ is hydrogen, alkyl containing 1 to 22 carbon atoms, phenyl, or phenyl substituted with one or more of alkyl containing 1 to 22 carbon atoms, halogen, and hydroxy;

$R^6$ is hydrogen or alkyl containing 1 to 22 carbon atoms, phenyl, or phenyl substituted with one or more of alkyl containing 1 to 22 carbon atoms, halogen, and hydroxy; or $R^6$ can be —C(O)OR$^8$ or —C(O)R$^8$ wherein $R^8$ is alkyl containing 1 to 22 carbon atoms; and $R^7$ is phenyl or alkyl containing 1 to 22 carbon atoms.

13. A method according to claim 12 wherein said peroxydicarbonate and diacyl peroxide compounds correspond to formula (IV)

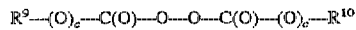

wherein $R^9$ and $R^{10}$ are independently aliphatic, cycloaliphatic or aromatic groups containing 1 to 22 carbon atoms, and c is zero or one.

14. A method according to claim 13 wherein in formula (IV) c is one.

15. A method according to claim 13 wherein in formula (IV) c is zero.

16. A method according to claim 13 wherein $R^9$ and $R^{10}$ are independently selected from the group consisting of phenyl, methyl, ethyl, n-propyl, isopropyl, n-butyl, sec-butyl, t-butyl, isobutyl, hexyl, octyl, neopentyl, 2-ethylhexyl, capryl, lauryl, myristyl, cetyl, stearyl, allyl, methallyl, crotyl, cyclohexyl, 4-t-butylcyclohexyl, 4-t-amylcyclohexyl, benzyl, 2-phenylethyl, 2-phenylbutyl, α-carbethoxyethyl, β-methoxyethyl, 2-phenoxyethyl, 2-methoxyphenyl, 3-methoxyphenyl, 2-ethoxyethyl, 2-ethoxyphenyl, 3-methoxybutyl, 2-carbamyloxyethyl, 2-chloroethyl, 2-nitrobutyl and 2-nitro-2-methylpropyl.

17. A method according to claim 12 wherein said stabilizer is selected from the group consisting of ethyl-2-cyclopentanone carboxylate, methyl-2-cycloheptanone carboxylate, ethyl-2-cyclohexanone carboxylate, 2-acetyl cyclopentanone, 2-acetyl cyclohexanone, ethyl-4-methyl-2-cyclohexanone-1-carboxylate, 1,3-cyclohexanedione, 1,3-cyclopentanedione, 2,4-pentanedione and dibenzoyl methane, and mixtures thereof.

18. A method according to claim 12 wherein the amount of said stabilizer is 0.2 to 5% by weight of said organic peroxide.

19. A method according to claim 12 wherein said stabilizer comprises a β-dicarbonyl compound of formula (I).

20. A method according to claim 12 wherein said stabilizer comprises a β-dicarbonyl compound of formula (II).

21. A method according to claim 12 wherein said stabilizer comprises a β-dicarbonyl compound of formula (III).

22. A method according to claim 12 wherein said organic peroxide component is selected from the group consisting of di-2-ethylhexyl peroxydicarbonate, di-sec-butyl peroxydicarbonate, diethyl peroxydicarbonate, di-n-butyl peroxydicarbonate, isopropyl-sec-butyl peroxydicarbonate, di-4-tert-butylcyclohexyl peroxydicarbonate, di-n-propyl peroxydicarbonate, di-isopropyl peroxydicarbonate, benzoyl peroxide, dilauroyl peroxide, didecanoyl peroxide, diacetyl peroxide, 2-methylpropionyl-3-methylpentanoyl peroxide, and di-(3,5,5-trimethylhexanoyl) peroxide and mixtures thereof.

* * * * *